United States Patent [19]

Ohyama et al.

[11] 4,420,486
[45] Dec. 13, 1983

[54] BENZOXAZOLONE DERIVATIVES, PROCESSES FOR PREPARATION THEREOF AND COMPOSITIONS CONTAINING THEM

[75] Inventors: Hiroshi Ohyama, Chigasaki; Kimiyoshi Kaneko, Isehara; Hiromichi Ishikawa, Atsugi; Sanae Takada, Atsugi; Ken Morita, Atsugi; Takuo Wada, Hatano; Masahiko Miyahara; Masazumi Arakawa, both of Atsugi, all of Japan

[73] Assignee: Hokko Chemical Industry Co., Ltd., Tokyo, Japan

[21] Appl. No.: 227,377

[22] Filed: Jan. 22, 1981

[51] Int. Cl.$^3$ .................... C07D 263/58; A01N 43/76
[52] U.S. Cl. .................................. 424/272; 548/221; 564/413
[58] Field of Search .................. 548/221; 424/272

[56] References Cited

U.S. PATENT DOCUMENTS

| 2,922,792 | 1/1960 | Model et al. | 548/221 |
|---|---|---|---|
| 2,922,794 | 1/1960 | Model et al. | 548/221 |
| 2,999,047 | 9/1961 | Model et al. | 424/272 |
| 3,190,797 | 6/1965 | Bindler et al. | 548/221 |
| 3,256,293 | 6/1966 | Baker et al. | 548/221 |

FOREIGN PATENT DOCUMENTS

| 1023627 | 1/1958 | Fed. Rep. of Germany | 548/221 |
|---|---|---|---|
| 1147007 | 4/1963 | Fed. Rep. of Germany | 548/221 |
| 926455 | 9/1959 | United Kingdom | 424/272 |
| 355008 | 6/1972 | U.S.S.R. | 548/221 |

OTHER PUBLICATIONS

Böshagen, H. et al., Chem. Ber., 103, 123–132, (1970).

*Primary Examiner*—Donald G. Daus
*Assistant Examiner*—S. A. Gibson
*Attorney, Agent, or Firm*—Larson and Taylor

[57] ABSTRACT

Certain new 5,6,7-trichlorobenzoxazolone derivatives are highly active against a wide range of plant fungal and bacterial diseases and have a reduced phytotoxicity. These derivatives are also useful to control the growth of various fungi and bacteria being capable of deteriorating industrial materials.

9 Claims, No Drawings

BENZOXAZOLONE DERIVATIVES, PROCESSES FOR PREPARATION THEREOF AND COMPOSITIONS CONTAINING THEM

FIELD OF THE INVENTION

This invention relates to new benzoxazolone derivatives, to processes for the preparation thereof, to fungicidal and bactericidal compositions containing the derivatives and to methods of combating various fungi and bacteria using the derivatives and the compositions.

BACKGROUND OF THE INVENTION

It is known in the art that certain benzoxazolone derivatives are useful as fungicides and bactericides for agricultural and horticultural purposes. For example, German Patent Specification No. 10 23 627 describes the anti-fungal and anti-bacterial properties of some benzoxazolone derivatives whose benzene ring bears a substituent such as 5-chloro, 5,6- ot 5,7-dichloro or 4,5,7-trichloro group but no alkyl substituent. German Patent Specification No. 11 47 007 discloses the antimicrobial properties of 4,5,6,7-tetrachlorobenzoxazolone, while U.S.S.R. Patent Specification No. 355,008 teaches such properties of 4,5,6-trichlorobenzoxazolene.

Further, Japanese Patent Publication No. 23519/65 describes the fungicidal and bactericidal properties of benzoxazolone derivatives of the formula:

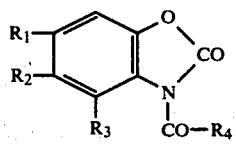

wherein $R_1 = R_2 = R_3 = H$; $R_1 = Cl$, $R_2 = R_3 = H$; $R_2 = Cl$, $R_1 = R_3 = H$; $R_1 = R_2 = Cl$, $R_3 = H$; or $R_1 = R_2 = R_3 = Cl$; and $R_4$ is phenyl optionally substituted by halogen, nitro, lower alkyl or lower alkoxy.

We have synthesized and carefully studied a variety of other new benzoxazolone derivatives in an attempt to develop new benzoxazolone microbicides which possess a low toxicity and good safety and exhibit a high activity against a wide range of fungi and bacteria. As a result, we have now discovered new benzoxazolone derivatives which have not been described in literatures and which are very useful as fungicides and bactericides. The derivatives of this invention carry three chlorine substituent at 5-, 6- and 7-positions of the benzene ring. Surprisingly, these 5,6,7-trichlorobenzoxazolone derivatives have been found to possess considerably improved fungicidal and bactericidal properties over those of known 4,5,7-trichlorobenzoxazolone and 4,5,6-trichlorobenzoxazolone as will be clearly seen from Examples hereinafter.

An object of this invention is to provide new benzoxazolone derivatives useful as anti-fungal and antibacterial agents for non-medical utility. Another object of the invention is to provide processes for the preparation of these benzoxazolone derivatives.

Further object of this invention is to provide fungicidal or bactericidal compositions for non-medical uses containing the derivatives as active ingredient. Still further object of the invention is to provide a method of combating fungi and bacteria using the derivatives or the compositions containing them.

Other objects and advantages of this invention will become apparent from the following description.

DETAILED DESCRIPTION OF THE INVENTION

According to this invention, there is provided a benzoxazolone compound of the general formula:

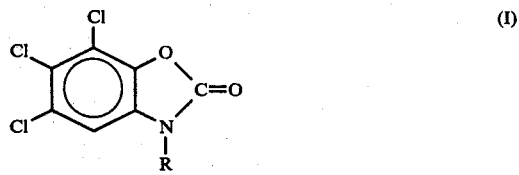

wherein R represents hydrogen atom or an alkyl, alkylcarbonyl, haloalkylcarbonyl, alkyloxycarbonyl, mono- or di-alkylaminocarbonyl, alkylsulfonyl, phenylsulfonyl or optionally substituted benzoyl or phenylaminocarbonyl group.

In general formula (I), R may be an alkyl group, particularly of 1-4 carbon atoms; an alkylcarbonyl group, particularly ($C_{1-4}$)alkylcarbonyl group; a haloalkylcarbonyl group, particularly chloro($C_{1-4}$)alkylcarbonyl group; an alkyloxycarbonyl group, particularly ($C_{1-4}$)alkyloxycarbonyl group; a mono- or di-alkylaminocarbonyl group, particularly mono- or di-($C_{1-4}$)alkylaminocarbonyl group; an alkylsulfonyl group, particularly ($C_{1-4}$)alkylsulfonyl group; or phenylsulfonyl group. R may also be an optionally substituted benzoyl group, including unsubstituted benzoyl group and sulstituted benzoyl group such as methylbenzoyl and chlorobenzoyl; as well as an optionally substituted phenylaminocarbonyl group, including unsubstituted phenylaminocarbonyl group and a substituted phenylaminocarbonyl group such as mono- or di-chlorophenylaminocarbonyl group.

A preferred group of the compounds include those of formula (I) in which R is an alkylcarbonyl, alkyloxycarbonyl or alkylsulfonyl group where the alkyl group contains 1 to 4 carbon atoms.

Specific examples of the compounds of this invention are listed in Table 1 below.

TABLE 1

| Compound No. | R | Melting Point (°C.) |
|---|---|---|
| 1 | H | 253-254 |
| 2 | $CH_3$ | 135-139 |
| 3 | $COCH_3$ | 171-172 |
| 4 | $COC_2H_5$ | 161-162 |
| 5 | $COC_4H_9-n$ | 111-112 |
| 6 | $COCH_2Cl$ | 187-188 |
| 7 | CO—⟨phenyl⟩ | 188-190 |

TABLE 1-continued

[Structure: trichloro benzoxazolone with N-R]

| Compound No. | R | Melting Point (°C.) |
|---|---|---|
| 8 | CO-C₆H₄-CH₃ (o-tolyl) | 198-200 |
| 9 | CO-C₆H₃(CH₃)₂ (dimethylphenyl) | 157-159 |
| 10 | COOCH₃ | 163-164 |
| 11 | CONHCH₃ | 173-175 |
| 12 | CON(CH₃)₂ | 127-129 |
| 13 | CONH-C₆H₅ | 164-165 |
| 14 | CONH-C₆H₃Cl₂ | 235-237 |
| 15 | SO₂CH₃ | 218-219 |
| 16 | SO₂-C₆H₅ | 197-198 |
| 17 | COOC₂H₅ | 99-100 |
| 18 | COOC₃H₇—n | 104-105 |
| 19 | COOC₃H₇—iso | 129-130 |

The compounds of this invention can be prepared by the reaction routes outlined in Schemes A, B and C as shown below and some of the compounds may be made by the method as shown in Scheme D hereinbelow:

Scheme A

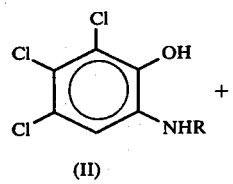

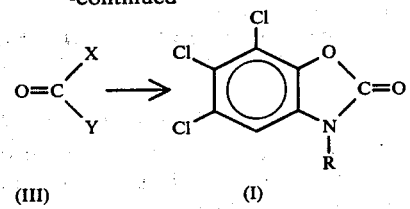

The group R in general formulae (I) and (II) has the same meanings as given hereinfefore. The compounds of formula (II) in which R is, for example acetyl group may be prepared in a high yield by acetylating orthoaminophenol in a conventional manner and then halogenating the acetylation product with three equivalents of chlorine. The compound thus obtained may be hydrolized, for example, with dilute hydrochloric acid to give the corresponding compound of formula (II) in which R is hydrogen atom. The latter compound can be alkylated or acylated by any conventional method to afford a variety of compounds (II).

In general formula (III), the symbols X and Y which may be the same or different each represents halogen, alkoxy, haloalkoxy, alkylthio or amino group. The compounds of formula (III) include phosgenic compounds such as phosgen and diphosgen (i.e. trichloromethyl chloroformate), haloformates, halothiolformates, carbonic diesters and urea.

According to Scheme A, it is generally believed that the compound (I) may be produced in two stages wherein compound HX or HY is eliminated upon the reaction between the compound (II) and the compound (III) to form an intermediate, which is further reacted with the compound (III) to allow further elimination of compound HX or HY, respectively. Thus, if a stable intermediate is formed depending upon the nature of the compounds (III) used, it may be isolated on the way and then cyclized to produce the final compound (I). Such stable intermediate may be formed in an alternative route without resort to the reaction between the compound (II) and the compound (III) and then cyclized to give the compound (I).

The reaction between the compounds (II) and (III) may be carried out in the absence of any solvent but preferably in the presence of an organic solvent which may possibly be an excess of the compound (III) itself. Examples of the solvent to be used include hydrocarbons, halogenated hydrocarbons, ethers, esters, acid amides, alcohols and dimethylsulfoxide, among which a suitable solvent will be selected for use depending upon the nature of the compounds (III). An acid-binding agent may be used to smoothly advance the reaction, as some of the compounds (III) may lead to the formation of an acid during the course of the reaction. The acid-binding agent to be used for this purpose includes organic amines such as triethylamine and pyridine and inorganic bases such as potassium carbonate. The reaction may be effected at ambient temperature, although it can be completed in a reduced period of time when carried out at an elevated temperature.

After the completion of the reaction, the object compound of formula (I) may be isolated and purified by any conventional method. For instance, a salt or salts of the acid-binding agent precipitated in the reaction mixture may be filtered off where the binder is used, and then the solvent be evaporated off from the filtrate to leave the compound (I). Alternatively, water and/or a suitable organic solvent such as benzene, chloroform, ether and tetrahydrofuran may be added to the reaction mixture to fractionally precipitate the object compound therefrom.

Particulars of the method according to Scheme A are given hereinafter in Examples 1–4.

Scheme B

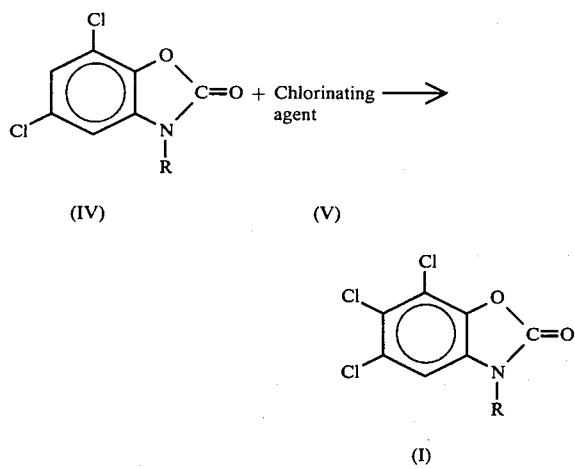

The group R in general formula (IV) is as defined hereinabove. The compound of formula (IV) in which R is hydrogen atom is known as described in U.S. Pat. No. 2,922,794. This compound can be alkylated or acylated in a conventional way to produce the corresponding N-substituted compound of formula (II). As the chlorinating agent (V), there can be used chlorine itself or sulfuryl chloride alone or combinations of hydrochloric acid and an oxidizing agent such as bleaching powder, potassium chlorate or manganese dioxide.

In Scheme B, the chlorination reaction is usually carried out in a solvent and at an elevated temperature to accelerate the reaction in the case where the chlorination is effected with chlorine or sulfuryl chloride. The solvent which may be used in that case includes water, acetic acid and halogenated hydrocarbons. If the halogenation is conducted using a combination of hydrochloric acid and an oxidizing agent such as bleaching powder, potassium chlorate or manganese dioxide, then the compound (IV) may be dissolved in the acid with subsequent addition of the powder of the oxidizing agent or a concentrated aqueous solution thereof. A solvent such as acetic acid may, if necessary, be used.

The presence of a catalyst, for example, iron, iron chloride, phosphorus compound, aluminium chloride or antimony chloride or the radiation of ultraviolet rays serves to smoothly advance the reaction of Scheme B.

After the completion of the reaction, the object compound (I) may be recovered from the reaction solution directly be evaporation of the solvent or possibly by addition to the reaction solution of water and/or an appropriate organic solvent such as benzene, chloroform, ether or tetrahydrofuran for the purpose of fractional extraction.

Particulars of the method according to Scheme B are indicated hereinafter in Examples 5 and 6.

Scheme C

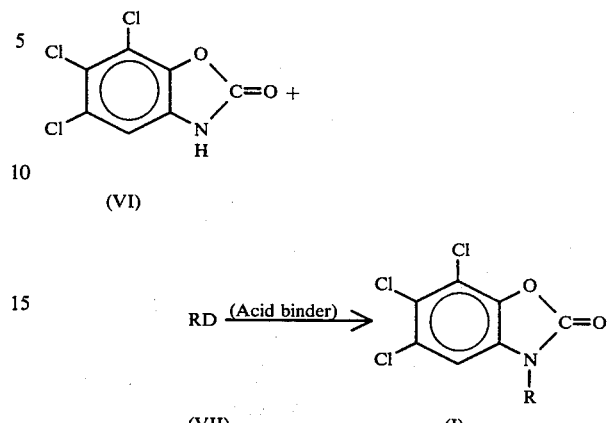

In formula (VII), R is one of the groups as defined hereinabove other than hydrogen atom and D stands for halogen atom. When the group R to be introduced in the starting compound (VI) is an alkyl group, the reagent of the formula (VII) may be a di-alkyl sulfate of the formula:

where R is an alkyl group. Thus, the compounds of formula (VII) may include alkyl halides, acyl halides and dialkyl sulfates. These compounds can easily be made by conventional methods known per se.

The reaction between the compound (VI) and the compound (VII) according to Scheme C may be carried out in the absence of any solvent but preferably in the presence of an organic solvent which may possibly be an excess of the compound (VII) itself. Examples of the solvent to be used include hydrocarbons, halogenated hydrocarbons, ethers, esters, ketones, acid amides, alcohols and dimetylsulfoxide. The acid binder for use in the reaction includes organic amines such as triethylamine and pyridine and inorganic bases such as potassium carbonate. The reaction may be effected at ambient temperature or conveniently at an elevated temperature. The reaction time to be required will, of course, depend on the nature of the compound (VII) used, the nature of the solvent if used and the reaction temperature employed, although it may be reduced when the reaction is performed in a polar organic solvent.

For recovery of the object compound after the completion of the reaction, the resulting reaction solution may be filtered to remove a salt of the acid binder precipitated therein and the filtrate be evaporated to leave the desired compound. In certain cases, water and/or a sultable organic solvent such as benzene, chlorofor, ether and tetrahydrofuran may be added to the reaction mixture to fractionally precipitate the object compound.

Particulars of the method according to Scheme C are given hereinafter in Examples 7–9.

Scheme D

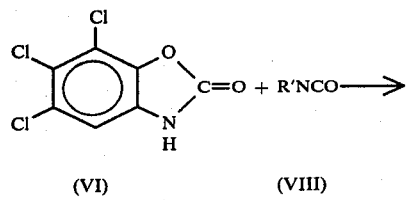

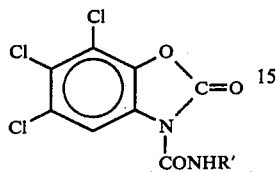

In formulae (VIII) and (IX), R' stands for alkyl group or optionally substituted phenyl group. Thus, the method as shown in Scheme D is available for the preparation of the compounds of formula (I) in which R represents alkylaminocarbonyl or optionally substituted phenylaminocarbonyl group.

The reaction between the compounds (VI) and (VIII) may be carried out in the absence of any solvent but preferably in the presence of an organic solvent which may possibly be an excess of the compound (VIII) itself. The solvent to be used must be inert to the compounds (VIII) under the reaction conditions and includes, for example, hydrocarbons, halogenated hydrocarbons, ethers, esters and ketones. If a small amount of an organic amine such as triethylamine or pyridine is present as catalyst, the reaction will proceed very smoothly. The reaction may be satisfactorily conducted at ambient temperature or possibly at an elevated temperature. The duration to be required for the reaction will depend upon the nature of the compound (VIII) used and other reaction conditions, although the reaction may be usually completed in a relatively short time.

After the completion of the reaction, the object compound can be isolated from the reaction mixture by filtering off the crystals of the compound precipitated or by evaporation of the solvent as the case may be.

The method according to Scheme D is illustrated in more detail with reference to Example 10.

According to a further aspect of this invention, therefore, there is provided a process for preparing a compound of general formula (I) according to claim 1, which comprises:

(a) reacting a compound of the formula:

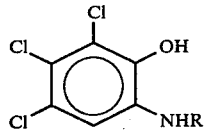

(II)

wherein R is, as defined in claim 1, with a carbonyl compound of the formula:

(III)

wherein X and Y, which may be the same or different, each represents halogen atom or alkoxy, haloalkoxy, alkylthio or amino group;

(b) chlorinating a compound of the formula:

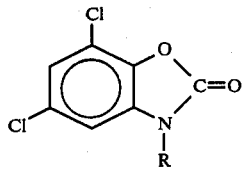

(IV)

wherein R is as defined in claim 1;

(c) reacting in the presence of an acid binder the compound of the formula:

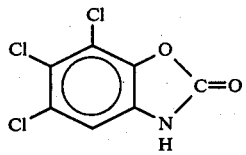

(VI)

with a compound of the formula:

RD (VII)

wherein R is as defined in claim 1 except for hydrogen atom and D represents halogen atom or with a di-alkyl sulfate of the formula:

where R is an alkyl group, to produce a compound of formula (I) in which R is other than hydrogen atom; or (d) reacting a compound of formula (VI) above with an isocyanate compound of the formula:

R'NCO (VII)

wherein R' represent alkyl or optionally substituted phenyl group to produce a compound of formula (I) in which R is a group of —CONHR'.

The compounds of this invention are highly active against a wide range of fungal and bacterial diseases, particularly including the following:
*Piricularia oryzae* (blast) on rice,
*Pellicularia sasaki* (sheathe blight) on rice,
*Cochliobolus miyabeanus* (brown spot) on rice,
*Xanthomonas oryzae* (bacterial leaf blight) on rice,
*Alternaria kikuchiana* (black spot) on pear,
*Glomerella cingulata* (ripe rot) on vine,
*Cladosporium fulvum* (leaf mold) on tomato,
*Phytophthora infestans* (late blight) on tomato,
*Sclerotinia sclerotiorum* (stem rot) on France bean,
*Sphaerotheca fuliginea* (powdery mildew) on cucumber,
*Fusarium oxysporum* (fusarium wilt) on cucumber,

*Psendoperonospora cubensis* (downy mildew) on cucumber,
*Colletotrichum lagenarium* (anthracnose) on cucumber,
*Erwinia aroidea* (soft rot) on Chinese cabbage.

Some of the compounds are significantly active as seed dressings, for example, against *Gibberella fujikuroi* (Bakanae disease) and *Cochliobolus miyabeanus* on rice.

The compounds of the invention are active not only to combat the fungal and bacterial diseases as mentioned above in the agricultural and horticultural applications but also to control the growth of various fungi and bacteria being capable of deteriorating industrial materials. Thus, where the compounds are applied to general industrial products such as point, wood, paper, pulp, textiles, cosmetics, leathers, ropes, plastics, rubbers and adhesives, it is possible to prevent the products from deterioration or decay which may otherwise be caused by the fungi and bacteria.

The compounds may be used as such for fungicidal and bactericidal purposes but are more conveniently formulated into compositions for such usage. This invention, therefore, also provides a fungicidal or bactericidal composition for non-medical uses comprising a compound of general formula (I) above as active ingredient, in association with a carrier or diluent for the active ingredient.

This invention further provides a method of controlling the growth of fungi and bacteria in a plant or an industrial material, which method comprises applying a compound of general formula (I) to the plant or the industrial material or to the locus of the plant which is infested or likely to become infested with the fungi and bacteria.

For the purposes as described above, the compounds of this invention are preferably used in the form of a composition. The type of the compositions used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, clay, powdered magnesia, Fuller's earth, gypsum, Hewitt's earth and diatomaceous earth. Compositions for dressing seed, for example, may comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable solvents are dimethylsulfoxide, dimethylformamide, formamide and aliphatic alcohols.

The compositions to be used as sprays may also be in the form of aerosols wherein the formulation is held in a container under pressure in the presence of a propellant, e.g. fluorotrichloromethane or dichlorodifluoromethane.

By including suitable additives, for example additives for improving the distribution, adhesive power and resistance to rain on treated surfaces, the different compositions can be better adapted for various utilities. The active ingredient can be used as mixtures with fertilisers (e.g. nitrogen- or phosphorus-containing fertilisers).

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-ionic agents.

Suitable cationic agents are quaternary ammonium compounds for example, cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates). Suitable non-ionic agents are the condensation products of ethylene oxide with fatty alcohols such as olely alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrolidone and sodium carboxymethylcellulose), and the vegetable gum (for example gum acacia and gum tragacanth).

The composition for use as aqueous dispersions or emulsions are generally supplied in the form of a concentrate containing a high proportion of the active ingredient, the concentrate to be diluted with water before use. These concentrates often should be able to withstand storage for prolonged periods and after such storage be capable of dilution with water in order to form aqueous preparations which remain homogenoeus for a sufficient time to enable them to be applied by conventional spray equipment. The concentrates may conveniently contain 10–95%, generally 25–60%, by weight of the active ingredient. When diluted to form aqueous preparations, such preparations may contain varying amounts of the active ingredient depending upon the intended purpose, but an aqueous preparation containing $1 \times 10^{-5}$% to 10% by weight of the active ingredient may be used.

When the composition of this invention is in the form of dusting powders or granules, the composition will generally be applied as such to the plants to be treated at a rate of 2 to 4 Kg per 10 ares (or at a rate of 10 to 1,000 g of active ingredient per 10 ares). Where the composition is in the form of wettable powder, emulsifiable concentrate or flowable preparation, it will usually be diluted with water before use to give an active ingredient concentration of 10 to 5,000 ppm, the dilute formulation being generally applied to the plants at a rate of 50 to 300 l per 10 ares. For treatment of industrial materials such dilute formulation comprising 10 to 5000 ppm of active ingredient will be applied at an appropriate rate which may vary over a wide range.

The compositions of this invention can comprise also one or more other compounds having biological activity, for example other known fungicides, bactericides, plant growth regulators, herbicides and insecticides. In particular, some of the compounds have been found to achieve a noticeable synergistic effect when used in admixture with certain known fungicides, as will be observed from the results given in Example 47 hereinafter.

Examples of fungicides and bactericides which may be used in admixture with the compounds of this invention include the following:

carbamate fungicides such as 3,3'-ethylenebis (tetrahydro-4,6-dimethyl-2H-1,3,5-thiadiazine-2-thione), zinc or manganese ethylenebis(dithiocarbamate), bis(dimethyldithiocarbamoyl)disulfide, zinc propylenebis (dithiocarbamate), bis(dimethyldithiocarbamoyl) ethylenediamine, nickel dimethyldithiocarbamate, methyl 1-(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate and 5-methyl-10-butoxycarbonylamino-10,11-dehydrodibenzo (b, f)azepine; pyridine fungicides such as zinc bis(1-hydroxy-2(1H) pyridinethionate) and 2-pyridinethiol-1-oxide sodium salt; phosphorus fungicides such as O,O-diisopropyl S-benzylphosphorothioate and O-ethyl S,S-diphenyldithiophosphate; phthalimide fungicides such as N-(2,6-diethylphenyl)phthalimide and N-(2,6- diethylphenyl)-4-methylphthalimide; dicarboxyimide fungicides such as N-trichloromethylthio-4-cyclohexene-1,2-dicarboxyimide and N-tetrachloroethylthio-4-cyclohexene-1,2-dicarboxyimide; oxathine fungicides such as 5,6-dihydro-2-methyl-1,4-oxathine-3-carboxanilido-4,4-dioxide and 5,6-dihydro-2-methyl-1,4-oxathine-3-carboxanilide, naphthoquinone fungicide such as 2,3-dichloro-1,4-naphthoquinone, 2-oxy-3-chloro-1,4-naphthoquinone copper sulfate; pentachloronitrobenzene; 1,4-dichloro-2,5-dimethoxybenzene; 5-methyl-S-triazol(3,4-b)benzthiazole; 2-(thiocyanomethylthio)benzothiazole; 3-hydroxy-5-methylisooxazole; N-2,3-dichlorophenyltetrachlorophthalamic acid; 5-ethoxy-3-trichloromethyl-1-2,4-thiadiazole; 2,4-dichloro-6-(O-chloroanilino)-1,3,5-triazine; 2,3-dicyano-1,4-dithioanthraquinone; copper 8-quinolinate; polyoxine; varidamycin; cycloheximide, iron methanearsonate; diisopropyl-1,3-dithiolane-2-iridene malonate; 3-allyloxy-1,2-benzoisothiazol-1,1-dioxide; kasugamycin; Blasticidin S; 4,5,6,7-tetrachlorophthalide; 3-(3,5-dichlorophenyl)-5-ethenyl-5-methyloxazolizine-2,4-dione; N-(3,5-dichlorophenyl)-1,2-dimethylcyclopropane-1,2-dicarboxyimide; S-n-butyl-5'-para-t-butylbenzyl-N-3-pyridyldithiocarbonylimidate; 4-chlorophenoxy-3,3-dimethyl-1-(1H,1,3,4-triazole-1-yl)-2-butanone; methyl-D,L-N-(2,6-dimethylphenyl)-N-(2'-methoxyacetyl)alaninate; N-propyl-N-[2-(2,4,6-trichlorophenoxy)ethyl]imidazol-1-carboxamide; N-(3,5-dichlorophenyl)succinimide; tetrachloroisophthalonitrile; 2-dimethylamino-4-methyl-5-n-butyl-6-hydroxypyrimidine; 2,6-dichloro-4-nitroaniline; 3-methyl-4-chlorobenzithiazol-2-one, 1,2,5,6-tetrahydro-4H-pyrrolo-[3,2,1-i,j]quinoline-2-one; 3'-isopropoxy-2-methylbenzanilide; 1-[2-(2,4-dichlorophenyl)-4-ethyl-1,3-dioxorane-2-ylmethyl]-1H,1,2,4-triazol; 1,2-benzisothiazoline-3-one; basic copper chloride; basic copper sulfate; N'-dichlorofluoromethylthio-N,N-dimethyl-N-phenylsulfamide; ethyl-N-(3-dimethylamino-propyl)thiocarbamate hydrochloride; piomycin; S,S-6-methylquinoxaline-2,3-diyldithiocarbonate; complex of zinc and maneb; dizinc bis(dimethyldithiocarbamate) ethylenebis(dithiocarbamate).

Examples of plant growth regulators and herbicides which may be used in combination with the compounds of this invention includes the following:

isourea plant growth regulators such as N-methoxycarbonyl-N'-4-methylphenylcarbamoylethylisourea and 1-(4-chlorophenylcarbamoyl)-3-ethoxycarbonyl-2-methylisourea; another type of plant growth regulators such as sodium naphthaleneacetate, 1,2-dihydropyridazine-3,6-dione and gibberellins; triazine herbicides such as 2-methylthio-4,6-bisethylamino-1,3,5-triazine, 2-chloro-4,6-bisethylamino-1,3,5-triazine, 2-methoxy-4-ethylamino-6-isopropylamino-1,3,5-triazine, 2-chloro-4-ethylamino-6-isopropylamino-s-triazine, 2-methylthio-4,6-bis(isopropylamino)-s-triazine and 2-methylthio-4-ethylamino-6-isopropylamino-s-triazine; phenoxy herbicides such as 2,4-dichlorophenoxyacetic acid and methyl, ethyl and butyl esters thereof, 2-chloro-4-methylphenoxyacetic acid, 4-chloro-2-methylphenoxyacetic acid and ethyl 2-methyl-4-chlorophenoxybutylate; diphenylether herbicides such as 2,4,6-trichlorophenyl-4'-nitrophenylether, 2,4-dichlorophenyl-4'-nitrophenylether and 3,5-dimethylphenyl-4'-nitrophenylether; urea herbicides such as 3-(3,4-dichlorophenyl)-1-methoxy-1-methyl urea, 3-(3,4-dichlorophenyl)-1,1-dimethylurea and 3-(4-chlorophenyl)-1,1-dimethyl urea; carbamate herbicides such as 3-methoxycarbonylaminophenyl-N-(3-methylphenyl)carbamate, isopropyl-N-(3-chlorophenyl)carbamate and methyl-N-(3,4'-dichlorophenyl)carbamate; uracil herbicides such as 5-bromo-3-sec-butyl-6-methyluracil and 1-cyclohexyl-3,5-propyleneuracil; thiolcarbamate herbicides such as S-(4-chlorobenzyl)-N,N-diethylthiolcarbamate, S-ethyl-N-cyclohexyl-N-ethylthiolcarbamate and S-ethyl-hexahydro-1H-azepine-1-carbothioate and S-ethyl-N,N-di-n-propylthiocarbamate; pyridinium herbicides such as 1,1'-dimethyl-4,4'-bispyridinium dichloride; phosphoric herbicides such as N-(phosphonomethyl)glycine; aniline herbicides such as L,L,L-trifluoro-2,6-dinitro-N,N-dipropyl-p-toluidine, 4-(methylsulfonyl)-2,6-dinitro-N,N-dipropylaniline and $N^3$, $N^3$-diethyl-2,4-dinitro-6-trifluoromethyl-1,3-phenylenediamine; acid anilide herbicides such as 2-chloro-2',6'-diethyl-N-(butoxymethyl)acetoanilide, 2-chloro-2',6'-diethyl-N-(methoxymethyl)acetoanilide, and 3,4-dichloropropioneanilide; pyrazole herbicides such as 1,3-dimethyl-4-(2,4-dichlorobenzoyl)-5-hydroxypyrazole and 1,3-dimethyl-4-(2,4-dichlorobenzoyl)-5-(p-toluenesulfonyloxy)pyrazole; 5-tert-butyl-3-(2,4-dichloro-5-isopropoxyphenyl)-1,3,4-oxadiazoline-2-one; 2-[N-isopropyl, N-(4-chlorophenyl)carbamoyl]-4-chloro-5-methyl-4-isooxazoline-3-one; 3-isopropyl-benzo-2-thia-1,3-diazinone-(4)-2,4-dioxide and 3-(2-methylphenoxy)pyridazine.

Examples of insecticides which may be mixed with the compounds of this invention include the following:

phosphoric insecticides such as O,O-diethyl O-(2-iropropyl-4-methyl-6-pyrimidinyl)phosphorothioate, O,O-diethyl S-2-[(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl)phosphorodithioate, O,O-dimethyl S-2-[(ethylthio)ethyl]phosphorodithioate, O,O-diethyl S-2-[(ethylthio)ethyl]phosphorodithioate, O,O-dimethyl-1-hydroxy-2,2,2-trichloroethylphosphonate, O,O-diethyl-O-(5-phenyl-3-isooxazolyl)phosphorothioate, O,O-dimethyl O-(2,5-dichloro-4-bromophenyl)phosphonothioate, O,O-dimethyl O-(3-methyl-4-methylmercaptophenyl)thiophosphate, O-ethyl O-p-cyanophenyl phenylphosphonothioate, O,O-dimethyl-S-(1,2-dicarboethoxyethyl)phosphorodithioate, 2-chloro-(2,4,5-trichlorophenyl)vinyldimethyl phosphate, 2-chloro-1-(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6-chloro-2-oxo-3-benzooxazolinyl)methyl]O,O-diethyl phosphorodithioate, 2-chloro-1-(2,4-dichlorophenyl)vinyl diethylphosphate, O,O-diethyl O-(3-oxo-2-phenyl-2H-pyridazine-6-yl)phosphorothioate, O,O-dimethyl S-(1-methyl-2-ethylsulfinyl)-ethyl phosphorothiolate, O,O-dimethyl S-phthalimidemethyl phosphorodithioate, O,O-diethyl S-(N-ethoxycarbonyl-N- methylcarbamoylmethyl)phosphorodithioate, O,O-dimethyl S-[2-methoxy-1,3,4-thiadiazol-5-(4H)-onyl-(4)-methyl]dithiophosphate, 2-methoxy-4H-1,3,2-benzooxaphosphorine 2-sulfide, O,O-diethyl O-(3,5,6-trichloro-2 pyridyl)-phosphorothioate, O-ethyl O-2,4-dichlorophenyl thionobenzene phosphonate, S-[4,6-diamino-s-triazine-2-yl-methyl]O,O-dimethyl phosphorodithioate, O-ethyl O-p-nitrophenyl phenylphosphonothioate, O,S-dimethyl N-acetyl phosphoroamidothioate, 2-diethylamino-6-methylpyrimidine-4-yl-diethylphosphorothionate, 2-diethylamino-6-methylpyrimidine-4-yl-dimethylphosphorothionate, O,O-diethyl O-p-(methylsulfinyl)phenyl phosphorothioate, O-ethyl S-propyl O-2,4-dichlorophenyl phosphorodithioate and cis-3-(dimethoxyphosphinoxy)N-methyl-cis-crotoneamide; carbamate insecticides such as 1-naphthyl N-methylcarbamate, S-methyl N-[(methylcarbamoyl)oxy]thioacetoimidate, m-tolyl methylcarbamate, 3,4-xylyl methylcarbamate, 3,5-xylyl methylcarbamate, 2-sec-butylphenyl N-methylcarbamate, 2,3-dihydro-2,2-dimethyl-7-benzofuranylmethylcarbamate, 2-isopropoxyphenyl N-methylcarbamate, 1,3-bis(carbamoylthio)-2-(N,N-dimethylamino)propanehydrochloride and 2-diethylamino-6-methylpyrimidine-4-yl-dimethylcarbamate; and another insecticides such as N,N-dimethyl N'-(2-methyl-4-chlorophenyl)formamidine hydrochloride, nicotine sulfate, milbemycin, 6-methyl-2,3-quinoxalinedithiocyclic S,S-dithiocarbonate, 2,4-dinitro-6-sec-butylphenyl dimethylacrylate, 1,1-bis(p-chlorophenyl)2,2,2-trichloroethanol, 2-(p-tert-butylphenoxy)isopropyl-2'-chloroethylsulfite, azoxybenzene, di-(p-chlorophenyl)-cyclopropyl carbinol, di[tri(2,2-dimethyl-2-phenylethyl)tin]oxide, 1-(4-chlorophenyl)-3-(2,6-difluorobenzoyl) urea and S-tricyclohexyltin O,O-diisopropylphosphorodithioate.

This invention is further illustrated but not limited by the following Example, in which % and parts are all by weight.

EXAMPLE 1

Preparation of compound No. 1 in Table 1 (Scheme A)

21.3 g of 2-amino-4,5,6-trichlorophenol, 27.6 g of anhydrous potassium carbonate and 150 ml of toluene were placed in a 300 ml round-bottom flask and 9.9 g of phosgen was slowly added to the mixture with stirring under cooling an ice-water bath. The resulting mixture was heated at reflux temperature for one hour and the reaction solution was then cooled and transferred to a 500 ml separating funnel. 150 ml of tetrahydrofuran and 150 ml of water were added into the funnel and the organic layer was separated, dried over anhydrous sodium sulfate and filtered. The filtrate was evaporated to remove the solvent, leaving yellowish white crystals. The crystals were recrystallized from a mixed solvent of methanol and acetone to give 22.7 g of 5,6,7-trichlorobenzoxazolone as white crystals having a melting point of 253°–254° C.

EXAMPLE 2

Preparation of compound No. 1 (Scheme A)

21.3 g of 2-amino-4,5,6-trichlorophenol, 27.6 g of anhydrous potassium carbonate and 150 ml of ethyl acetate were placed in a 300 ml round-bottom flask and a solution of 9.9 g of diphosgen (trichloromethyl chloroformate) dissolved in 50 ml of ethyl acetate was added dropwise to the mixture with stirring under cooling on ice-water bath. The resulting mixture was heated at reflux temperature for one hour and the reaction solution was then cooled and subjected to suction filtration to remove insoluble salts. The filtrate was concentrated to dryness under reduced pressure to afford yellowish white crystals, which were recrystallized from methanol/acetone to give 19.6 g of 5,6,7-trichlorobenzoxazolone as white crystals with a melting point of 253°–254° C.

EXAMPLE 3

Preparation of compound No. 1 (Scheme A)

18.1 g 2-ethoxycarbonylaminophenol (made from 2-aminophenol and ethyl chloroformate) was dissolved in 200 ml of acetic acid and 23.4 g of gaseous chlorine was passed into the solution at a temperature of 80°–90° C. The reaction solution thus obtained was cooled and evaporated to remove the acetic acid, leaving 27.9 g of yellow crystals of 2-ethoxycarbonylamino-4,5,6-trichlorophenol which melted at 190°–193° C.

The crystals were placed, together with 45 ml of dimethylformamide and 0.5 g of anhydrous potassium carbonate, into a 200 ml round-bottom flask and the mixture was heated with stirring at 140° C. for 4 hours. After cooling the resultant solution, 100 ml of water was added to the latter to precipitate crystals, which were then separated by suction filtration and dried in air for 2 hours to afford pale yellow crystals. Recrystallization from methanol/acetone gave 19.1 g of white crystals of 5,6,7-trichlorobenzoxazolone with a melting point of 253°–254° C.

EXAMPLE 4

Preparation of compound No. 3 in Table 1 (Scheme A)

10.9 g of o-aminophenol and 100 ml of acetic acid were placed in a 300 ml round-bottom flask, followed by addition of 10.2 g acetic anhydride under ice-water cooling. The mixture was heated at 60° C. for one hour to complete the reaction, resulting in formation of 2-acetaminophenol. 23.4 g gaseous chlorine was then passed into the reaction mixture at a temperature of 80°–90° C. and the resulting reaction solution was cooled and evaporated under reduced pressure to leave 24.9 g of yellow crystals of 2-acetamino-4,5,6-trichlorophenol which melted with decomposition at 200° C.

The crystals were placed in a 300 ml round-bottom flask, to which was added 150 ml of tetrahydrofuran followed by 9.6 g of sodium hydride (50% suspension in oil). 9.9 g of phosgen was then introduced into the mixture under ice-water cooling and the resultant mixture was agitated at room temperature for one hour. The reaction solution was transferred to a 500 ml separating funnel, into which were added 150 ml of benzene and 150 ml of water and the organic layer was separated, dried over anhydrous sodium sulfate and filtered. The filtrate was evaporated to remove the solvent, leaving yellow crystals. The crystals were recrystallized from a mixed solvent of hexane and acetone to give 25.2 g of N-acetyl-5,6,7-trichlorobenzoxazolone as white crystals having a melting point of 171°–172° C.

EXAMPLE 5

Preparation of compound No. 1 (Scheme B)

20.4 g of 5,7-dichlorobenzoxazolone and 150 ml of acetic acid were placed in a 300 ml round-bottom flask and the mixture was heated to 80°–90° C., followed by passage of 7.8 g of gaseous chlorine. The reaction solution was concentrated by evaporation of the acetic acid to yield yellow crystals. Recrystallization from methanol/acetone gave 23.4 g of white crystals of 5,6,7-trichlorobenzoxazolone with a melting point of 253°–254° C.

EXAMPLE 6

Preparation of compound No. 3 (Scheme B)

24.6 g of N-acetyl-5,7-dichlorobenzoxazolone and 150 ml of chloroform were placed in a 300 ml round-bottom flask, to which was then added 16.5 g of sulfuryl chloride at ambient temperature. The mixture was heated at reflux temperature for two hours and the reaction solution so obtained was evaporated under reduced pressure to leave yellow crystals. Recrystallization from hexane/acetone gave 26.6 g of white crystals of N-acetyl-5,6,7-trichlorobenzoxazolone with a melting point of 171°–172° C.

EXAMPLE 7

Preparation of compound No. 2 in Table 1 (Scheme C)

4.8 g of 5,6,7-trichlorobenzoxazolone, 2.8 g of anhydrous potassium carbonate, 2.5 g of dimethyl sulfate and 50 ml of acetone were charged in a 100 ml sound-bottom flask and the contents of the flask were heated under reflux for 2 hours. Subsequently, the reaction solution was evaporated under reduced pressure and the residue was taken up in 50 ml of water. The yellowish brown crystals deposited were collected by filtration and recrystallized from acetone to give 4.8 g of yellow crystals of N-methyl-5,6,7-trichlorobenzoxazolone with a melting point of 135°–139° C.

EXAMPLE 8

Preparation of compound No. 7 in Table 1 (Scheme C)

4.8 g of 5,6,7-trichlorobenzoxazolone, 2.0 g of triethylamine and 50 ml of acetone were placed in a 100 ml round-bottom flask, into which was then added dropwise 2.8 g of benzoyl chloride under ice-water cooling and stirring. After completion of the addition, the resultant mixture was heated under reflux for one hour to accomplish the reaction whereupon the reaction solution was allowed to cool and filtered to remove the precipitated salts. The filtrate was evaporated to leave white crystals, which were recrystallized from hexane/acetone to give 6.5 g of white crystals of N-benzoyl-5,6,7-trichlorobenzoxazolone with a melting point of 188°–190° C.

EXAMPLE 9

Preparation of compound No. 10 in Table 1 (Scheme C)

Following the same procedure as described in Example 8 except that the benzoyl chloride was replaced by 1.9 g of methyl chloroformate, 5.7 g of N-methoxycarbonyl-5,6,7-trichlorobenzoxazolone was obtained as yellowish white crystals of m.p. 163°–164° C.

EXAMPLE 10

Preparation of compound No. 14 in Table 1 (Scheme D)

4.8 g of 5,6,7-trichlorobenzoxazolone, 3.8 g of 3,5-dichlorophenylisocyanate, 50 ml of acetone and three drops of triethylamine were placed in a 100 ml round-bottom flask and the mixture was agitated at ambient temperature for one hour. The precipitate was separated by filtration to give 7.7 g of light yellow crystals which were identified as N-3,5-dichlorophenylcarbamoyl-5,6,7-trichlorobenzoxazolone of m.p. 235°–237° C.

EXAMPLE 11

Emulsifiable concentrate formulation

An emulsifiable concentrate comprising 20% of the active ingredient was made up by uniformly mixing the ingredients set out below and stirring the mixture until all the ingredients were dissolved.

|  | Parts |
| --- | --- |
| Compound No. 10 | 20 |
| Dimethylformamide | 30 |
| Xylene | 35 |
| Polyoxyethylene alkyl aryl ether | 15 |

EXAMPLE 12

Oil formulation

An oil formulation was made up by mixing 10 parts of compound No. 1 and 90 parts of ethyl cellosolve (2-ethoxyethanol) and stirring the mixture until these ingredients were dissolved.

EXAMPLE 13

Flowable formulation

A flowable formulation comprising 40% of the active ingredient was prepared by uniformly mixing together the following ingredients:

|  | Parts |
| --- | --- |
| Compound No. 4 (ground to particle sizes below 10μ) | 40 |
| Lauryl sulfate | 2 |
| Sodium alkylnaphthalene sulfonate | 2 |
| Hydroxypropyl cellulose | 1 |
| Water | 55 |

EXAMPLE 14

Water-dispersible powder formulation

A water-dispersible powder was made by uniformly mixing the ingredients listed below and then grinding the mixture.

|  | Parts |
| --- | --- |
| Compound No. 3 | 20 |
| polyoxyethylene alkyl aryl ether | 5 |
| Calcium lignosulfonate | 3 |
| Kieselguhr | 72 |

EXAMPLE 15

Dusting powder formulation

A dusting powder was made up by uniformly mixing the ingredients set out below and grinding the resultant mixture.

|  | Parts |
| --- | --- |
| Compound No. 5 | 3 |
| Fine powder of silicic anhydride | 0.5 |
| Calcium stearate | 0.5 |
| Clay | 50 |
| Talc | 46 |

EXAMPLE 16

Granular formulation

A composition in the form of granules was prepared by uniformly mixing the ingredients set out below and then granulating the mixture in the presence of added water. The resultant mixture was dried and passed through a sieve to obtain the desired size of grains.

|  | Parts |
| --- | --- |
| Compound No. 6 | 5 |
| Calcium lignosulfonate | 1 |
| Bentonite | 30 |
| Clay | 64 |

EXAMPLE 17

Wettable powder formulation

A wettable powder was made by uniformly mixing the ingredients listed below and grinding the mixture.

|  | Parts |
| --- | --- |
| Compound No. 10 | 20 |
| N—trichloromethylthio-4-cyclohexene-1,2-dicarboximide | 20 |
| Polyoxyethylene alkyl aryl ether | 5 |
| Calcium lignosulfonate | 3 |
| Kieselguhr | 52 |

EXAMPLE 18

In this Example, the benzoxazolone derivatives of this invention were tested against a variety of fungal and bacterial diseases of plants.

The tests were conducted according to standard agar dilution method. The culture medium employed was potato-dextrose agar medium (pH 5.8) for fungi and bouillon agar medium (pH 7.0) for bacteria. The medium containing an acetone solution of the required concentration of the active ingredient was inoculated by means of a platinum loop with a spore suspension obtained by adding sterilized water to test microorganisms which had been incubated on a slant of the medium in a test tube. Further incubation on the inoculated medium was carried out for 48 hours at 24° C. for fungi and at 28° C. for bacteria. Then, the growth of the microorganisms was observed and the minimum inhibitory concentrations (MIC, μg/ml) of the derivatives under test were determined.

The test results are shown in Table 2 below. In Tables given hereinafter, controls A,B,C and D indicate the use as the active ingredient of the following compounds disclosed in the literatures noted:

A: 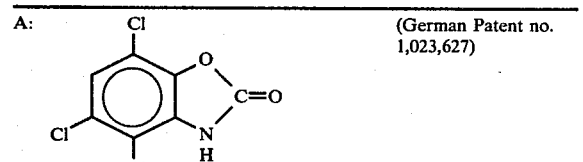 (German Patent no. 1,023,627)

B: 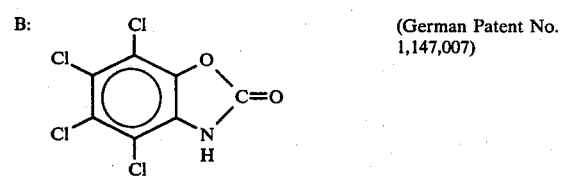 (German Patent No. 1,147,007)

C: 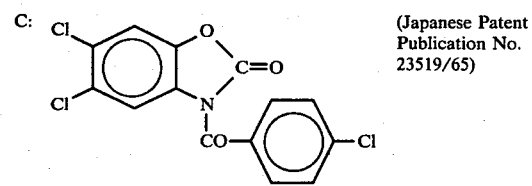 (Japanese Patent Publication No. 23519/65)

D: 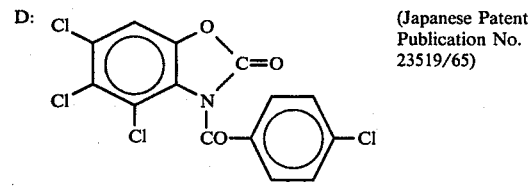 (Japanese Patent Publication No. 23519/65)

TABLE 2

| Disease and Plant | Compound No. in Table 1 MIC (μg/ml) | | | | | | | | | | | | | | | | | | | MIC (μg/ml) | | | |
|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | A | B | C | D |
| *Fusarium oxysporum* (Cucumber) | <2.5 | <2.5 | <2.5 | <2.5 | <2.5 | <2.5 | <5 | <5 | <5 | <2.5 | <2.5 | <5 | <5 | <5 | <2.5 | <5 | <2.5 | <2.5 | <2.5 | <20 | <20 | <20 | <20 |
| *Cladosporium fulvum* (Tomato) | <2.5 | <5 | <2.5 | <2.5 | <5 | <2.5 | <5 | <5 | <5 | <2.5 | <2.5 | <5 | <5 | <5 | <2.5 | <5 | <2.5 | <2.5 | <5 | <20 | <20 | <20 | <20 |
| *Gibberella fujikuroi* (Rice) | <2.5 | <2.5 | <2.5 | <2.5 | <2.5 | <2.5 | <2.5 | <2.5 | <2.5 | <2.5 | <2.5 | <2.5 | <2.5 | <2.5 | <2.5 | <2.5 | <2.5 | <2.5 | <2.5 | <20 | <20 | <20 | <20 |
| *Glomerella cingulata* (Vine) | <1.25 | <2.5 | <2.5 | <2.5 | <2.5 | <2.5 | <2.5 | <2.5 | <2.5 | <2.5 | <2.5 | <5 | <5 | <5 | <2.5 | <5 | <2.5 | <2.5 | <2.5 | <20 | <20 | <20 | <20 |
| *Alternaria kikuchiana* (Pear) | <5 | <5 | <5 | <5 | <5 | <5 | <5 | <5 | <10 | <5 | <5 | <5 | <5 | <5 | <5 | <5 | <5 | <5 | <5 | <40 | <40 | <40 | <40 |
| *Piricularia oryzae* (Rice) | <1.25 | <1.25 | <1.25 | <1.25 | <1.25 | <1.25 | <2.5 | <5 | <5 | <1.25 | <1.25 | <2.5 | <2.5 | <2.5 | <1.25 | <2.5 | <1.25 | <1.25 | <1.25 | <20 | <20 | <20 | <20 |
| *Cochliobolus miyabeanus* (Rice) | <2.5 | <2.5 | <2.5 | <2.5 | <2.5 | <2.5 | <2.5 | <2.5 | <5 | <1.25 | <1.25 | <5 | <5 | <5 | <1.25 | <5 | <1.25 | <1.25 | <1.25 | <20 | <20 | <20 | <20 |
| *Erwinia aroidea* (Chinese cabbage) | <2.5 | <5 | <5 | <5 | <5 | <5 | <10 | <20 | <20 | <2.5 | <5 | <10 | <10 | <10 | <2.5 | <10 | <5 | <20 | <20 | <160 | <80 | <80 | <80 |
| *Pseudomonas lachrymans* (Cucumber) | <10 | <10 | <10 | <10 | <10 | <10 | <20 | <20 | <20 | <10 | <10 | <10 | <10 | <10 | <5 | <10 | <10 | <10 | <20 | <160 | <80 | <160 | <80 |
| *Xanthomonas oryzae* (Rice) | <10 | <10 | <10 | <10 | <10 | <10 | <20 | <20 | <20 | <10 | <10 | <20 | <10 | <5 | <10 | <10 | <10 | <10 | <10 | <40 | <40 | <40 | <40 |

EXAMPLE 32

This Example illustrates the funjicidal activity of the benzoxazolone derivatives against *Piricularia oryzae* (blast on rice).

A water-dispersible powder formulation prepared as described in Example 27 was diluted with water to make up test formulations containing the required concentrations of the active ingredient. The test formulation was applied onto aquatic rice seedlings ("Asahi" variety, three-foilage stage) which had been soil-cultured in biscuit pots of 9 cm diameter in a greenhouse. One day after application, the treated seedlings were inoculated were inoculated by spraying with a spore suspension of *Piricularia oryzae* and incubation in a moist chamber of a relative humidity of 95–100% and a temperature of 24°–25° C. 5 Days after inoculation, the number of blast lesions per leaf at the three-foliage stage was evaluated and disease control was calculated by the following equation:

Disease control (%) =

$$\left(1 - \frac{\text{Number of lesions in treated plots}}{\text{Number of lesions in untreated plots}}\right) \times 100$$

The disease control is an average valve of the results of the test which were conducted in two replicates at each concentration of the active ingredient. The phytotoxicity towards rice plants was also assessed visually by the following grading:

| Grading | Extent of phytotoxicity |
| --- | --- |
| 5 | Severe damage |
| 4 | Great damage |
| 3 | Moderate damage |
| 2 | Light damage |
| 1 | Slight damage |
| 0 | No damage |

The test results are shown in Table 3 below.

TABLE 3

| Compound No. | Concentration (ppm) | Disease Control (%) | Phytotoxicity |
| --- | --- | --- | --- |
| 1 | 200 | 100 | 0 |
| 2 | " | 78 | 0 |
| 3 | " | 100 | 0 |
| 4 | " | 98 | 0 |
| 5 | " | 94 | 0 |
| 6 | " | 98 | 0 |
| 7 | " | 98 | 0 |
| 8 | " | 100 | 0 |
| 9 | 200 | 96 | 0 |
| 10 | " | 100 | 0 |
| 11 | " | 100 | 0 |
| 12 | " | 92 | 0 |
| 13 | " | 86 | 0 |
| 14 | " | 82 | 0 |
| 15 | " | 98 | 0 |
| 16 | " | 98 | 0 |
| 17 | " | 100 | 0 |
| 18 | " | 100 | 0 |
| 19 | " | 100 | 0 |
| Control A | " | 52 | 1 |
| Control B | " | 63 | 2 |
| Control C | " | 30 | 1 |
| Control D | " | 30 | 1 |
| IBP (Control)* | 480 | 75 | 0 |

TABLE 3-continued

| Compound No. | Concentration (ppm) | Disease Control (%) | Phytotoxicity |
| --- | --- | --- | --- |
| Untreated | — | 0 | — |

*IBP: 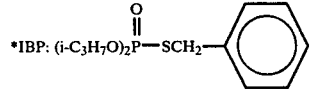

EXAMPLE 20

This Example illustrates the activity of the benzoxazolone derivatives against *Cochliobolus miyabeanus* (brown spot on rice).

The tests were carried out of the same procedure as in Example 19 except that rice seedlings at the four-foliage stage were inoculated with a spore suspension of *Cochliobolus miyabeanus*.

The results are set out in Table 4 below.

TABLE 4

| Compound No. | Concentration (ppm) | Disease Control (%) | Phytotoxicity |
| --- | --- | --- | --- |
| 1 | 500 | 100 | 0 |
| 2 | " | 85 | 1 |
| 3 | " | 100 | 0 |
| 4 | " | 98 | 0 |
| 5 | " | 96 | 0 |
| 6 | " | 100 | 0 |
| 7 | " | 94 | 0 |
| 8 | " | 92 | 0 |
| 9 | " | 88 | 0 |
| 10 | " | 100 | 0 |
| 11 | " | 98 | 0 |
| 12 | " | 94 | 1 |
| 13 | " | 90 | 0 |
| 14 | " | 92 | 1 |
| 15 | " | 86 | 0 |
| 16 | " | 83 | 0 |
| 17 | " | 100 | 0 |
| 18 | " | 100 | 0 |
| 19 | " | 100 | 0 |
| Control A | " | 32 | 3 |
| Control B | " | 54 | 4 |
| Control C | " | 25 | 1 |
| Control D | " | 30 | 1 |
| Triazine* (Control) | " | 93 | 0 |
| Untreated | — | 0 | — |

*Triazine: 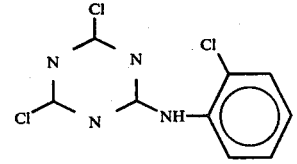

EXAMPLE 21

In this Example the active compounds were tested against *Sclerotinia sclerotiorum* (stem rot on French bean) by the following technique.

A water-dispersible powder formulation prepared as described in Example 14 was diluted with water to make up test formulations containing the required concentrations of the active ingredient. The test formulation was applied onto seedlings of French bean ("Taisho Kintoki" variety) at the two-true leaf stage which had been soil-cultured in biscuit pots of 9 cm diameter in a greenhouse. The rate of application was 10 ml of the formulation per pot. One day later, each leaflet of the two true leaves was inoculated at its centre with a piece of fungi-infected agar obtained by boring by means of a 5 mm cork borer the edge of the colony of *Sclerotinia sclerotiorum* fungus which had been incubated in potato-dextrose agar medium at 20° C. for two days. The inoculated seedlings were then kept in a humid room at 20° C. for three days to allow the disease development. Thereafter, the length of stem rot lesions was measured with a vernier caliper and disease control was calculated by the following equation:

Disease control (%) =

$$\left(1 - \frac{\text{Length of lesions in treated plots}}{\text{Length of lesions in untreated plots}}\right) \times 100$$

The disease control is an average value of the results of the tests which were conducted in two replicates at each concentration of the active ingredient. The phytotoxicity to French bean was visually assessed by the same grading as noted in Example 32.

The results are given in Table 5 below.

TABLE 5

| Compound No. | Concentration (ppm) | Disease Control (%) | Phytotoxicity |
|---|---|---|---|
| 1 | 500 | 100 | 1 |
| 3 | " | 88 | 0 |
| 5 | " | 86 | 0 |
| 6 | " | 94 | 1 |
| 10 | " | 100 | 0 |
| 17 | " | 89 | 0 |
| 19 | " | 85 | 0 |
| Control A | " | 43 | 3 |
| Control B | " | 48 | 4 |
| Control C | " | 26 | 2 |
| Control D | " | 20 | 2 |
| CNA* (Control) | " | 72 | 0 |
| Untreated | — | 0 | — |

*CNA: 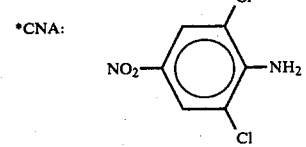

EXAMPLE 22

This Example illustrates the fungicidal effect of some of the benzoxazolone derivatives as seed dressings against *Cochlioblus miyabeanus* (brown spot on rice).

10 g of rice seeds ("Asaminori" variety) infected with the disease were packed in a Saron net sack and placed in a 50 ml beaker, where they were dipped at 15° C. for 24 hours in a dilute formulation added (made up as described in Example 21) in the same amount as that of the rice seeds. The seeds were then removed from the formulation and dipped in deionized water at 15° C. over a period of 5 days, after which they were allowed to germinate at 30° C. for 24 hours. The rice seeds being germinated were sown on the soil of black volcanic ashes (incorporating 4.5 g of ammonium sulfate, 6 g of calcium superphosphate and 1.5 g of potassium chloride) in plant pads (30×60×10 cm). The pads were then kept for growth in a greenhouse at 28° C.

20 Days after sowing (at the three-foilage stage), assessment was visually made of the extent of disease attack on the seedlings in each treated plot in terms of the following grading:

| Grading | Extent of disease attack |
|---|---|
| Slight | Disease attack observed only in very small part of primary leaf or in leaf sheath |
| Moderate | Primary leaf almost changed into brown color and killed in association with brown lesions on the primary and secondary true leaves. |
| Severe | Significantly poor growth of the seedlings which have been bent and changed into brown color with kill. |

The percentage of disease attack (attack rate) was determined from the overall seedlings evaluated as gradings "severe" and "moderate" and the seed-dressing (or seed-disinfection) rate was culculated by the following equation:

Seed-dressing rate (%) =

$$\left(1 - \frac{\text{Attack rate in treated plots}}{\text{Attack rate in untreated plots}}\right) \times 100$$

The Seed-dressing rate is a mean value of the results of the test which were conducted in two replicates at each concentration of the active ingredient. The phytotoxicity to rice plants was visually assessed by the same grading as noted in Example 19.

The results are given in Table 6 below.

TABLE 6

| Compound No. | Concentration (ppm) | Seed-dressing Rate (%) | Phytotoxicity |
|---|---|---|---|
| 1 | 500 | 98 | 1 |
| 3 | " | 97 | 0 |
| 10 | " | 96 | 0 |
| 11 | " | 98 | 0 |
| 14 | " | 92 | 0 |
| Control A | " | 63 | 2 |
| Control B | " | 72 | 3 |
| Control C | " | 40 | 1 |
| Control D | " | 40 | 1 |
| TMTD* (Control) | 2000 | 70 | 0 |
| Untreated | — | 0 | 0 |

*TMTD: 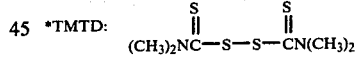

EXAMPLE 23

The benzoxazolone derivatives were tested on their seed-dressing activity against *Gibberella fujikuroic* (Bakanae disease on rice).

The test procedure employed was the same as described in Example 22 except that rice seeds ("Reimei" variety) naturally infected with the disease were used and that visual assessment was made 26 days after sowing (at the four-foliage stage).

The results are shown in Table 7 below.

TABLE 7

| Compound No. | Concentration (ppm) | Seed-dressing Rate (%) | Phytotoxicity |
|---|---|---|---|
| 1 | 500 | 98 | 1 |
| 3 | " | 100 | 0 |
| 10 | " | 98 | 0 |
| 11 | " | 96 | 1 |
| 14 | " | 88 | 0 |
| 17 | " | 90 | 0 |
| 18 | " | 88 | 0 |
| 19 | " | 92 | 0 |

TABLE 7-continued

| Compound No. | Concentration (ppm) | Seed-dressing Rate (%) | Phytotoxicity |
| --- | --- | --- | --- |
| Control A | " | 47 | 0 |
| Control B | " | 42 | 3 |
| Benomyl* (Control) | " | 98 | 0 |
| Untreated | — | 0 | — |

*Benomyl:

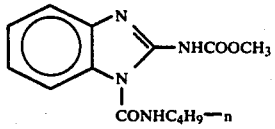

EXAMPLE 24

In this Example, the benzoxazolone derivatives were tested against *Phytophthora infestans* (late blight on tomato).

Dilute suspensions of a wettable powder containing the required concentrations of the active ingredient were prepared as described in Example 21. The test suspension was applied at a rate of 10 ml per pot onto young seedlings of tomato ("Sekaiichi" variety) at the three-true leaf stage which had been soil-cultured in biscuit pots of 9 cm diameter in a greenhouse. Spores of *Phytophthora infestans* which had been produced on potato tubers were suspended in sterilized water to give a spore concentration at which 20–30 spores were detectable within one sight under a microscope of 150 magnification.

One day after application, the leaves of the tomato seedlings were inoculated with drops of the spore suspension and the seedlings were then kept at 20° C. in a humid room to allow development of the disease. 3 Days later, the seedlings were removed from the room and the number of attacked leaves was counted. The percentage of attacked leaves and disease control were calculated by the following equations:

Percentage of attacked leaves =

$$\frac{\text{Number of attacked leaves}}{\text{Number of inoculated leaves}} \times 100$$

Disease control (%) =

$$\left(1 - \frac{\text{Percentage of attacked leaves in treated plots}}{\text{Percentage of attacked leaves in untreated plots}}\right) \times 100$$

The phytotoxicity towards tomato plants, was also evaluated by the same grading as defined in Example 19. The results are set out in Table 8 below.

TABLE 8

| Compound No. | Concentration (ppm) | Disease Control (%) | Phytotoxicity |
| --- | --- | --- | --- |
| 1 | 500 | 100 | 0 |
| 3 | " | 92 | 0 |
| 4 | " | 97 | 0 |
| 6 | " | 99 | 0 |
| 7 | " | 94 | 0 |
| 10 | " | 98 | 0 |
| 11 | " | 88 | 0 |
| 13 | " | 99 | 0 |
| 14 | " | 99 | 0 |
| 15 | " | 96 | 0 |
| 18 | " | 97 | 0 |
| 19 | " | 99 | 0 |
| Control A | " | 0 | 0 |

TABLE 8-continued

| Compound No. | Concentration (ppm) | Disease Control (%) | Phytotoxicity |
| --- | --- | --- | --- |
| Control B | " | 0 | 0 |
| Control C | " | 0 | 0 |
| Control D | " | 0 | 0 |
| Maneb* (Control) | " | 87 | 0 |
| Untreated | — | 0 | — |

*Maneb:

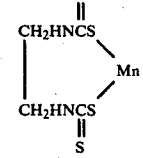

EXAMPLE 25

This Example illustrates the activity of the derivatives against *Sphaerotheca fuliginea* (powdery mildew on cucumber).

The dilute formulation prepared as in Example 24 was applied at a rate of 10 ml per pot onto cucumber seedlings ("Sagamihanjiro" variety) at the one-leaf stage which had been soil-cultured in biscuit pots of 9 cm diameter in a greenhouse. On the following day the seedlings were inoculated by spraying with a spore suspension of *Sphaerotheca fuliginea*. Ten days after inoculation, assessment was made of the percentage of lesion area on the seedlings and disease control was calculated by the following equation:

Disease control (%) =

$$\left(1 - \frac{\text{Percentage of lesion area in treated area}}{\text{Percentage of lesion area in untreated plots}}\right) \times 100$$

The results are tabulated in Table 9 below.

TABLE 9

| Compound No. | Concentration (ppm) | Disease Control (%) | Phytotoxicity |
| --- | --- | --- | --- |
| 1 | 200 | 92 | 0 |
| 4 | " | 95 | 0 |
| 5 | " | 92 | 0 |
| 8 | " | 90 | 0 |
| 9 | " | 90 | 0 |
| 10 | " | 96 | 0 |
| 11 | " | 92 | 0 |
| 18 | " | 90 | 0 |
| 19 | " | 98 | 0 |
| Control A | " | 20 | 1 |
| Control B | " | 10 | 1 |
| Control C | " | 10 | 1 |
| Control D | " | 13 | 1 |
| Dimethirimol* (Control) | " | 95 | 0 |
| Untreated | — | 0 | — |

*Dimethirimol:

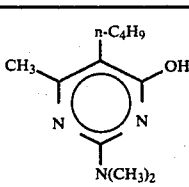

EXAMPLE 26

The benzoxazolone derivatives were tested against *Pseudoperonospora cubensis* (downy mildew on cucumber).

The dilute formulation prepared as in Example 24 was applied at a rate of 10 ml per pot to the back faces of leaves of cucumber young seedlings ("Sagamihanjiro" variety) at the one-true leaf stage which had been soil-cultured in biscuit pots of 9 cm diameter in a greenhouse. Spores of *Pseudoperonospora cubensis* which had been produced on cucumber leaves in a disease-development environment were brushed away into deionized water containing 50 ppm of Tween 20 (trade name of polyoxyethylene sorbitan monolaurate, product of Kao Atlas Co.) so as to give an inoculum having a spore concentration at which 20-30 spores were detectable within one sight under a microscope of 150 magnification.

One day after application, the leaves of the cucumber seedlings were inoculated on their treated lower surface by spraying with the inoculum. After completion of the inoculation, the seedlings were first placed in a humid room at 20° C. and then kept in a greenhouse at 24° C. to allow development of the disease. Six days later, the seedlings were removed from the greenhouse and assessment was made of the percentage of lesion area per pot. Disease control (%) was calculated by the equation as indicated in Example 38 and phytotoxicity to cucumber plants was evaluated by the same grading as in Example 19.

The test results are set out in Table 10 below.

TABLE 10

| Compound No. | Concentration (ppm) | Disease Control (%) | Phytotoxicity |
|---|---|---|---|
| 1 | 500 | 100 | 0 |
| 3 | " | 98 | 0 |
| 7 | " | 90 | 0 |
| 10 | " | 100 | 0 |
| 11 | " | 95 | 0 |
| 13 | " | 100 | 0 |
| 14 | " | 100 | 0 |
| 18 | " | 100 | 0 |
| 19 | " | 100 | 0 |
| Control A | " | 20 | 1 |
| Control B | " | 25 | 1 |
| Control C | " | 30 | 1 |
| Control D | " | 36 | 1 |
| Maneb (Control) | " | 90 | 0 |
| Untreated | — | 0 | — |

EXAMPLE 27

The benzoxazolone derivatives were tested against *Collectotrichum lagenarium* (anthracnose on cucumber).

The dilute formulation prepared as in Example 24 was applied at a rate of 10 ml per pot to the leaves of cucumber young seedlings ("Sagamihanpaku" variety) at the one-true leaf stage which had been soil-cultured in biscuit pots of 9 cm diameter in a greenhouse. Spores of *Collectotrichum lagenarium* produced by incubation on an oatmeal-agar medium at 24° C. for 10 days were suspended in sterilized water containing 50 ppm of Tween 20 so as to give a suspension of a spore concentration at which about 100 spores were detectable within one sight under a microscope of 150 magnification.

One day after application, the treated leaves of the cucumber seedlings were inoculated by spraying with the aforesaid spore suspension. The seedlings thus inoculated were subsequently treated in the same way as noted in Example 26 and disease control was calculated by the following equation:

$$\text{Disease control (\%)} = \left(1 - \frac{\text{Number of lesions in treated plots}}{\text{Number of lesions in untreated plots}}\right) \times 100$$

The results are shown in Table 11 below.

TABLE 11

| Compound No. | Concentration (ppm) | Disease Control (%) | Phytotoxicity |
|---|---|---|---|
| 1 | 500 | 100 | 0 |
| 3 | " | 98 | 0 |
| 7 | " | 96 | 0 |
| 10 | " | 100 | 0 |
| 19 | " | 100 | 0 |
| Control A | " | 45 | 1 |
| Control B | " | 37 | 1 |
| Control C | " | 35 | 1 |
| Control D | " | 43 | 1 |
| TPN* (Control) | " | 98 | 0 |
| Untreated | — | 0 | — |

*TPN:

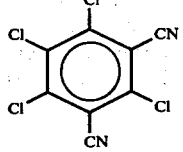

EXAMPLE 28

This Example illustrates the activity of the benzoxazolone derivatives against *Puccinia recondita* (leaf rust on wheat).

The dilute formulation prepared as in Example 24 was applied at a rate of 20 ml per three pots to wheat young seedlings ("Norin No. 61" variety) at the one-true leaf stage which had been soil-cultured in biscuit pots of 9 cm diameter in a greenhouse. Uredosorus of *Puccinia recondita* which had been produced on wheat leaves was brushed away into sterilized water containing 50 ppm of Tween 20 so as to give an inoculum of a spore suspension having a pore concentration at which Ca. 50 spores were detectable within one sight under a microscope of 150 magnification.

One day after application, the wheat seedlings were inoculated by spraying with the inoculum. After completion of the inoculation, the seedlings were first kept overnight in a humid room at 20° C. and then transferred into a greenhouse at 20° C. to allow development of the disease. Ten days after inoculation, the number of fungal uredosori with the disease developed per leaf was counted and disease control was calculated by the equation:

$$\text{Disease control (\%)} = \left(1 - \frac{\text{Number of uredosori in treated plots}}{\text{Number of uredosori in untreated plots}}\right) \times 100$$

The phytotoxicity to wheat plants was evaluated by the same grading as defined in Example 19. The results are given in Table 12 below.

TABLE 12

| Compound No. | Concentration (ppm) | Disease Control (%) | Phytotoxicity |
|---|---|---|---|
| 1 | 200 | 100 | 0 |
| 3 | " | 92 | 0 |
| 8 | " | 90 | 0 |
| 10 | " | 100 | 0 |
| 19 | " | 98 | 0 |
| Control A | " | 10 | 1 |
| Control B | " | 5 | 0 |
| Control C | " | 10 | 1 |
| Control D | " | 5 | 0 |
| Maneb (Control) | " | 96 | 0 |
| Untreated | — | 0 | — |

EXAMPLE 29

In this Example the benzoxazolone derivatives were tested against fungi and bacteria being capable of deteriorating industrial materials.

The tests were conducted following the agar dilution method as described in Example 28, but the incubation was performed for 3 days at 28° C. for fungi and at 30° C. for bacteria. The tests were carried out in two replicates at each concentration of the active compound under test and a mean value of the minimum inhibitory concentrations (MIC) was determined.

The results are set forth in Table 13 below.

TABLE 13

| Test Micro-organisms | Compound No. MIC (μg/ml) | | | | | |
|---|---|---|---|---|---|---|
| | 1 | 2 | 3 | 4 | 5 | 6 |
| Escherichia coli | <1.25 | <5 | <1.25 | <1.25 | <2.5 | <1.25 |
| Bacillus subtillis | <1.25 | <5 | <1.25 | <2.5 | <5 | <1.25 |
| Alcaligenes viscoluktis | <1.25 | <5 | <1.25 | <1.25 | <2.5 | <1.25 |
| Pseudomonas aeruginosa | <1.25 | <10 | <5 | <5 | <5 | <5 |
| Aspergillus niger | <1.25 | <10 | <1.25 | <2.5 | <2.5 | <2.5 |
| Penicillium citrinum | <1.25 | <5 | <1.25 | <2.5 | <2.5 | <1.25 |
| Rhizopus nigricans | <1.25 | <10 | <2.5 | <2.5 | <5 | <2.5 |
| Cladosporium herbarum | <1.25 | <5 | <1.25 | <1.25 | <2.5 | <1.25 |
| Chaetomium globosum | <1.25 | <5 | <1.25 | <1.25 | <1.25 | <1.25 |

| Test Micro-organisms | Compound No. MIC (μg/ml) | | | | | |
|---|---|---|---|---|---|---|
| | 7 | 8 | 9 | 10 | 11 | 12 |
| Escherichia coli | <5 | <5 | <5 | <1.25 | <1.25 | <2.5 |
| Bacillus subtilis | <5 | <5 | <5 | <1.25 | <2.5 | <2.5 |
| Alcaligenes viscoluktis | <5 | <5 | <5 | <1.25 | <1.25 | <1.25 |
| Pseudomonas aeruginosa | <5 | <10 | <10 | <2.5 | <2.5 | <2.5 |
| Aspergillus niger | <5 | <10 | <5 | <1.25 | <1.25 | <2.5 |
| Pencillium citrinum | <5 | <5 | <5 | <1.25 | <1.25 | <2.5 |
| Rhizopus nigricans | <10 | <10 | <10 | <2.5 | <1.25 | <2.5 |
| Cladosporium herbarum | <5 | <5 | <10 | <1.25 | <1.25 | <2.5 |
| Chaetomium globosum | <10 | <10 | <10 | <2.5 | <2.5 | <5 |

TABLE 13-continued

| Test Micro-organisms | Compound No. MIC (μg/ml) | | | | | |
|---|---|---|---|---|---|---|
| | 13 | 14 | 15 | 16 | 17 | 18 |
| Escherichia coli | <5 | <5 | <1.25 | <5 | <1.25 | <5 |
| Bacillus subtilis | <5 | <5 | <2.5 | <5 | <1.25 | <1.25 |
| Alcaligenes viscoluktis | <2.5 | <5 | <2.5 | <5 | <5 | <5 |
| Pseudomonas aeruginosa | <5 | <10 | <2.5 | <5 | <5 | <5 |
| Aspergillus niger | <5 | <10 | <5 | <10 | <1.25 | <2.5 |
| Penicillium citrinum | <5 | <10 | <2.5 | <5 | <1.25 | <2.5 |
| Rhizopus nigricans | <5 | <5 | <2.5 | <5 | <5 | <5 |
| Cladosporium herbarum | <10 | <10 | <2.5 | <5 | <1.25 | <2.5 |
| Chaetomium globosum | <10 | <10 | <5 | <5 | <5 | <5 |

| Test Micro-organisms | MIC (μg/ml) | | | | | |
|---|---|---|---|---|---|---|
| | Compound No. 19 | A | B | C | D | Proxel* |
| Escherichia coli | <1.25 | <40 | <20 | <40 | <40 | <10 |
| Bacillus subtilis | <1.25 | <40 | <40 | <40 | <20 | <10 |
| Alcaligenes viscoluktis | <1.25 | <40 | <20 | <20 | <20 | <10 |
| Pseudomonas aeruginosa | <5 | <80 | <40 | <40 | <40 | <20 |
| Aspergillus niger | <1.25 | <80 | <80 | <80 | <40 | <20 |
| Penicillium citrinum | <1.25 | <40 | <40 | <40 | <80 | <10 |
| Rhizopus nigricans | <5 | <160 | <80 | <80 | <80 | <20 |
| Cladosporium herbarum | <1.25 | <80 | <40 | <80 | <40 | <10 |
| Chaetomium globosum | <2.5 | <40 | <40 | <40 | <40 | <20 |

*Proxel:

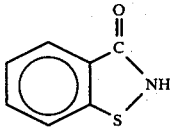

EXAMPLE 30

This Example illustrates the resistance to fungal growth of paints containing the benzoxazolone derivative.

The tests were carried out according to the method of JIS Z-2911 as follows: A given amount of an oil formulation prepared as in Example 12 was added to a white paint based on polyvinyl acetate emulsion and the resultant mixture was stirred for 30 seconds in a homogenizer to prepare a paint formulation, in which was dipped a filter paper ("Toyo Filter Paper" No. 2) of 12 cm diameter. The paper was then removed from the paint formulation and dried in air, when the amount of the paint deposited on the paper was adjusted to give a dry paint loading of 99–100% based on the weight of the filter paper. The dried paper was cut into a size of 3 cm diameter to make a circular specimen, which was then sticked onto the centre of an agar plate medium in a petri dish. Both the medium and the specimen were inoculated by spraying with each 1 ml of a mixed spore suspension made by mixing together equal amounts of respective spore suspensions of the three fungi (Aspergillus niger, Penicillium lutenum and Trichoderma T-1)

which had been separately incubated on a potato-dextrose agar medium.

Subsequently, the petri dish was capped and kept in an incubator at 28° C. for one week to allow incubation of the fungi, after which the growth of the fungi on the specimen was assessed on the grading of 3, 2 or 1 in which:

3 indicates no mycelial growth on the surface of the specimen, 2 indicates that the mycelial growth area does not exceed one-third on the surface of the specimen, and 1 indicates that the mycelial growth area exceeds one-third on the surface of the specimen.

TABLE 14

| Compound No. | Proportion of Compound to Solid Content of Paint (%) | Grading for Fungal Resistance |
|---|---|---|
| 1 | 0.15 | 3 |
| 3 | " | 3 |
| 10 | " | 3 |
| 11 | " | 3 |
| 15 | " | 3 |
| Control A | " | 2 |
| Control B (Control) | " | 2 |
| TBTO* (Control) | " | 2 |
| Untreated | — | 1 |

*TBO (Used in the form of emulsion) $(n\text{-}C_4H_9)_3SnO$

EXAMPLE 31

This Example illustrates the slime-controlling effect of the benzoxazolone derivatives.

An amount of routine water from a paper mill was taken in flask, into which was added an aqueous solution of the compound under test to give a concentration of 10 ppm of the active ingredient in the routine water. Before addition of the formulation and 0.5, 1, 2, 4 and 8 hours after addition of the formulation, bacterial colony counts in the routine water were determined by agar dilution plate method as follows: A sample of the routine water was diluted with sterilized saline solution and 1 ml of the dilute solution was placed in a petri dish. A dissolved bouillon agar medium was poured into and blended with the dilute solution. After incubation in the plate at 30° C. for 2 days, the bacterial colony was counted by means of a colonycounter and the bacterial count per ml of the routine water was calculated taking account of the multiplicity for dilution with the sterilized saline solution.

The tests were conducted in two replicates and a mean bacterial count was determined. The results are given in Table 15 below.

EXAMPLE 32

This Example illustrates the effectiveness of the benzoxazolone derivatives as wood preservatives.

A log of Cryptmerica japonica (Japanese "Sugi") of about 15 cm diameter and 60 cm long which had been dried to its fiber saturation point was sealed at its both transverse sections with an epoxy resin including glass wools. An oil formulation prepared as in Example 12 was diluted with water to 2% concentration of the active ingredient and then injected under a pressure of 15 kg/cm² into the wood over 3 hours. Thereafter, the wood was dried in air to reduce its water content to atmospheric humidity. Specimens of 2×2×1 cm size were taken from the dried wood and from a log wood of the same species treated with known wood preservatives as controls and all the specimens were dried in air for two weeks.

These specimens were then exposed to weathering conditions using an ultraviolet carbon-arc weatherometer over a period of two months (corresponding to six years under natural environmental conditions); namely the specimens were watered at a rate of 2100±100 mm/min. under a hydraulic pressure of 1.0 kg/cm² for 18 minutes after irradiation with ultraviolet rays for 2 hours and these operations were repeated in succession during said period. The specimens were then dried at a temperature of 60°±2° C. for 48 hours and weighed (the dry weight is denoted as $W_1$).

Subsequently, the specimens were subjected to preservation test according to the method of JIS A 9302. In this test, the specimens were inoculated with Coriolellus palustria or Coriolus versicolor which had been cultivated at 26° C. for 15 days on a sand medium containing 4% glucose. 0.3% peptone and 1.5% malt extract. After incubation at 26° C. for 90 days, the mycelia and other deposits were removed from the speciments, which were then air-dried for 24 hours, further dried at 60° C. for 48 hours and weighed (the dry weight is denoted as $W_2$).

The weight loss of the specimens is calculated by the equation:

$$\text{Weight loss (\%)} = \frac{W_1 - W_2}{W_1} \times 100$$

Preservation effectiveness (P.E.) is evaluated by the following equation:

$$P.E. = \left(1 - \frac{\text{Mean weight loss in treated plots}}{\text{Mean weight loss in untreated plots}}\right) \times 100$$

TABLE 15

| Compound No. | Bacteria per ml of Routine Water Interval between Addition of Compound and Evaluation (Hr) | | | | | |
|---|---|---|---|---|---|---|
| | Before Addition | 0.5 | 1 | 2 | 4 | 8 |
| 1 | $5.1 \times 10^7$ | $3.8 \times 10^2$ | $6.2 \times 10^2$ | $8.1 \times 10^2$ | $6.5 \times 10^2$ | $5.7 \times 10^2$ |
| 3 | " | $4.0 \times 10^2$ | $6.8 \times 10^2$ | $8.0 \times 10^2$ | $7.4 \times 10^2$ | $6.3 \times 10^2$ |
| 10 | " | $4.1 \times 10^2$ | $7.2 \times 10^2$ | $9.6 \times 10^2$ | $8.8 \times 10^2$ | $7.5 \times 10^2$ |
| MBT* (Control) | " | $4.3 \times 10^3$ | $1.2 \times 10^4$ | $3.2 \times 10^4$ | $1.2 \times 10^5$ | $4.8 \times 10^6$ |
| Proxel* (Control) | " | $5.1 \times 10^2$ | $9.1 \times 10^2$ | $3.1 \times 10^3$ | $7.1 \times 10^3$ | $9.0 \times 10^3$ |

*MBT: Methylenebisthiocyanate
**Proxel: 1,2-Benzisothiazolin-3-one

The test results are given in Table 16 below.

TABLE 16

| Compound No. | P.E. Value |
|---|---|
| 1 | 100 |
| 3 | 98 |
| 10 | 96 |
| Control A | 40 |
| PCP—Na* | 63 |
| Creosote oil | 95 |

*Sodium pentachlorophenolate

EXAMPLE 33

This Example illustrates the synergistic effect to be brought about by mixing certain compound of this invention with other known fungicides.

Wettable powder formulations containing compound No. 10 and other fungicides which were prepared as described in Example 17 were diluted with water to the required concentrations of the active ingredients. Using the dilute formulations the tests were carried out against Pseudoperonospora cubensis (cucumber), Sphaerotheca fuliginea (cucumber) and Sclerotinia sclerotiorum (French bean) by the procedures as noted in, respectively, Examples 26, 25 and 21 hereinbefore.

By way of reference, further tests were conducted in the same way using similar dilute formulations containing compound No. 10 alone or other fungicides alone.

Concentration and disease control of compound No. 10 alone (A) were 25 ppm and 26% for Pseudoperonospora cubensis, 50 ppm and 24% for Sphaerotheca fuliginea and 50 ppm and 26% for Sclerotinia sclerotiorum.

The results of the tests with other known fungicides alone (B) and mixed fungicides (A+B) are summarized in Table 17, 18 and 19 below.

TABLE 17

Activity against Pseudoperonospora cubensis

| | Single Fungicide (B) | | Mixed Fungicides | |
|---|---|---|---|---|
| Chemical | Concentration (ppm) | Disease Control (%) | Concentration Rate A + B | Disease Control (%) |
| N—Trichloromethylthio-4-cyclohexene-1,2-dicarboximide | 25 | 28 | 25 + 25 | 78 |
| Tetrachloroisophthalonitrile | " | 35 | 25 + 25 | 86 |
| Manganese ethylenebis(dithiocarbamate) | " | 38 | 25 + 25 | 87 |
| Zinc complex of manganese ethylenebis(dithiocarbamate) | " | 32 | 25 + 25 | 84 |
| Dizinc bis(dimethyldithiocarbamate) ethylenebis(dithiocarbamate) | " | 33 | 25 + 25 | 83 |
| Basic copper chloride | 50(as Cu) | 29 | 25 + 50 | 85 |
| Basic copper sulfate | 50(as Cu) | 24 | 25 + 50 | 81 |
| Copper 8-hydroxyquinolinate | 50 | 28 | 25 + 50 | 78 |
| Methyl DL-N—(2,6-dimethylphenyl)-N—(2'-methoxyacetyl)alanilate | 5 | 38 | 25 + 5 | 87 |
| Ethyl N—(3-dimethylaminopropyl) thiocarbamate hydrochloride | 10 | 30 | 25 + 10 | 80 |

TABLE 18

Activity against Sphaerotheca fuliginea

| | Single Fungicide (B) | | Mixed Fungicide | |
|---|---|---|---|---|
| Chemical | Concentration (ppm) | Disease Control (%) | Concentration Rate A + B | Disease Control (%) |
| 1,2-Bis(3-methoxycarbonyl-2-thioureido) benzene | 5 | 32 | 50 + 5 | 80 |
| Methyl 1-(n-butylcarbamoyl)-2-benzimidazolecarbamate | 5 | 34 | 50 + 5 | 83 |
| 1-[(2-(2,4-Dichlorophenyl)-4-ethyl-1,3-oxorane-2-yl)methyl]-1H-1,2,4-triazolepiomycin | 1 | 40 | 50 + 1 | 88 |
| | 10 | 32 | 50 + 10 | 87 |
| 4-Chlorophenoxy-3,3-dimethyl-1-(1H-1,3,4-triazol-1-yl)2-butanone | 1 | 34 | 50 + 1 | 81 |
| S—n-Butyl-s'-p-t-butylbenzyl-N-3-pyridyldithiocarboximidate | 1 | 40 | 50 + 1 | 87 |
| N—Propyl-N—[2-(2,4,6-trichlorophenoxy)ethyl]-imidazol-1-carboxamide | 5 | 27 | 50 + 5 | 78 |
| 2-Dimethylamino-4-methyl-5-n-butyl-6-hydroxypyrimidine | 5 | 26 | 50 + 5 | 74 |
| 6-Methylquinoxaline-2,3-dithiocarbonate | 5 | 28 | 50 + 5 | 84 |

TABLE 19

Activity against Sclerotinia sclerotirum

| | Single Fungicide (B) | | Mixed Fungicides | |
|---|---|---|---|---|
| Chemical | Concentration (ppm) | Disease Control (%) | Concentration Rate A + B | Disease Control (%) |
| N'—Dichlorofluoromethylthio-N,N—dimethyl-N'—phenylsulfamide | 50 | 26 | 50 + 50 | 77 |
| 2,6-Dichloro-4-nitroaniline | 50 | 26 | 50 + 50 | 79 |
| N—(3,5-Dichlorophenyl)-1,2-dimethylcyclopropane-1,2-dicarboximide | 12.5 | 40 | 50 + 12.5 | 89 |
| 3-(3,5-Dichlorophenyl)-5-ethenyl-5-methyl-2,4-oxazolidine-dione | 12.5 | 36 | 50 + 12.5 | 85 |
| 1-Isopropylcarbamoyl-3-(3,5-dichlorpenyl) hydantoin | 12.5 | 38 | 50 + 12.5 | 87 |
| Polyoxine | 25 | 32 | 50 + 25 | 82 |
| N—Tetrachloroethylthio-4-cyclohexene-1,2-dicarboximide | 25 | 36 | 50 + 25 | 85 |

What we claim is:

1. A 5,6,7-trichlorobenzoxazolone compound of the formula

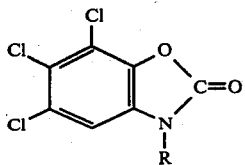

wherein R is hydrogen, a ($C_1$-$C_4$) alkyl, a ($C_1$-$C_4$)alkylcarbonyl, a chloro ($C_1$-$C_4$)alkylcarbonyl, a ($C_1$-$C_4$)alkyloxycarbonyl, a mono- or di-($C_1$-$C_4$)alkylaminocarbonyl, a ($C_1$-$C_4$)alkylsulfonyl or phenylsulfonyl.

2. 5,6,7-Trichlorobenzoxazolone.

3. N-Acetyl-5,6,7-trichlorobenzoxazolone.

4. A compound selected from the group consisting of N-methoxycarbonyl-5,6,7-trichlorobenzoxazolone, N-ethoxycarbonyl-5,6,7-trichlorobenzoxazolone and N-isopropoxycarbonyl-5,6,7-trichlorobenzoxazolone.

5. A compound selected from the group consisting of N-methanesulfonyl-5,6,7-trichlorobenzoxazolone and N-phenylsulfonyl-5,6,7-trichlorobenzoxazolone.

6. A fungicidal or bactericidal composition for non-medical uses comprising as active ingredient an effective amount of a compound of formula (I) as defined in claim 1 in association with an inert carrier or diluent for the active ingredient.

7. A fungicidal or bactericidal composition according to claim 1 in the form of a concentrate comprising 10 to 95% by weight of the active ingredient.

8. A fungicidal or bactericidal composition according to claim 1 in the form of a dilute formulation comprising $1 \times 10^{-5}$ to 10% by weight of the active ingredient.

9. A method of controlling the growth of fungi and bacterial in a plant or an industrial material, which method comprises applying an effective amount a compound of formula (I) as defined in claim 1 to the plant or the industrial material or to the locus of the plant which is infested or likely to become infested with the fungi and bacteria.

* * * * *